(12) United States Patent
Stopek

(10) Patent No.: US 8,268,958 B2
(45) Date of Patent: Sep. 18, 2012

(54) PHOSPHOLIPID COPOLYMERS

(75) Inventor: Joshua Stopek, Guilford, CT (US)

(73) Assignee: Tyco Healthcare Group IP, Mansfield, MA (US)

( * ) Notice: Subject to any disclaimer, the term of this patent is extended or adjusted under 35 U.S.C. 154(b) by 0 days.

(21) Appl. No.: 13/075,772

(22) Filed: Mar. 30, 2011

(65) Prior Publication Data

US 2011/0178201 A1    Jul. 21, 2011

Related U.S. Application Data

(63) Continuation-in-part of application No. 12/145,605, filed on Jun. 25, 2008.

(60) Provisional application No. 60/964,856, filed on Aug. 15, 2007.

(51) Int. Cl.
*C08G 63/08*    (2006.01)

(52) U.S. Cl. ...... 528/354; 523/105; 525/287; 525/326.6

(58) Field of Classification Search .................... 528/354
See application file for complete search history.

(56) References Cited

U.S. PATENT DOCUMENTS

| | | |
|---|---|---|
| 3,187,752 A | 6/1965 | Glick |
| 3,565,077 A | 2/1971 | Glick |
| 4,014,973 A | 3/1977 | Thompson |
| 4,043,344 A | 8/1977 | Landi et al. |
| 4,047,533 A | 9/1977 | Perciaccante et al. |
| 4,300,565 A | 11/1981 | Rosensaft et al. |
| 4,954,593 A | 9/1990 | Vara et al. |
| 5,019,093 A | 5/1991 | Kaplan et al. |
| 5,059,213 A | 10/1991 | Chesterfield et al. |
| 5,133,738 A | 7/1992 | Korthoff et al. |
| 5,181,923 A | 1/1993 | Chesterfield et al. |
| 5,226,912 A | 7/1993 | Kaplan et al. |
| 5,261,886 A | 11/1993 | Chesterfield et al. |
| 5,290,548 A | 3/1994 | Goldberg et al. |
| 5,306,289 A | 4/1994 | Kaplan et al. |
| 5,318,575 A | 6/1994 | Chesterfield et al. |
| 5,370,031 A | 12/1994 | Koyfman et al. |
| 5,376,400 A | 12/1994 | Goldberg et al. |
| 5,383,387 A | 1/1995 | Chesterfield et al. |
| 5,662,682 A | 9/1997 | Chesterfield et al. |
| 5,667,528 A | 9/1997 | Colligan |
| 5,804,263 A | 9/1998 | Goldberg et al. |
| 5,885,566 A | 3/1999 | Goldberg |
| 6,087,462 A | 7/2000 | Bowers et al. |
| 6,090,901 A | 7/2000 | Bowers et al. |
| 6,203,564 B1 | 3/2001 | Hutton et al. |
| 6,225,431 B1 | 5/2001 | Bowers et al. |
| 6,284,854 B1 | 9/2001 | Bowers et al. |
| 6,387,379 B1 | 5/2002 | Goldberg et al. |
| 7,160,953 B2 | 1/2007 | Bowers et al. |
| 7,300,990 B2 | 11/2007 | Lewis et al. |
| 2002/0165205 A1 | 11/2002 | Kubo et al. |
| 2003/0157193 A1 | 8/2003 | McDonald et al. |
| 2005/0208093 A1 | 9/2005 | Glauser et al. |
| 2006/0160985 A1 | 7/2006 | Pacetti et al. |
| 2006/0193884 A1 | 8/2006 | Stopek et al. |
| 2007/0032666 A1 | 2/2007 | Read et al. |
| 2008/0033106 A1 | 2/2008 | Koroskenyi et al. |

FOREIGN PATENT DOCUMENTS

| | | |
|---|---|---|
| EP | 0496813 B | 12/1994 |
| EP | 1498420 A | 1/2005 |
| WO | WO 2007/133782 A1 | 11/2007 |

OTHER PUBLICATIONS

European Search Report for EP 08 252691.4-2102 date of completion is Oct. 31, 2008 (10 pages).
Iwakaki Y; Tojo Y: Kurosaki T; Nakabayashi : "Reduced Adhesion of Blood Cells to Biodegradable Polymers by Introducing Phosphorylcholine Moieties" Journal of Biomedical Materials Research Part A, vol. 65a, 2003, pp. 164-169, XP002502022.
Meng S; Zhong W; Chou L L; Wang Q; Liu Z; Du Q: "phosphorylcholine end-capped poly-[epsilon]-caprolactone: A Novel Biodegradable Material With Improved Antiadsorption Property" Journal of Applied Polymer Science, vol. 103, Jan. 15, 2007 pp. 989-997, XP002502023.
Watanabe J; Ishihara K: "Change in cell adhesion property on cytocompatible interface using phospholipid polymer grafted with poly(D,L-lactic acid) segment for tissue engineering" science and technology of advanced materials, vol. 4, 2003, pp. 539-544, XP002502024.
Watanabe J; Ishihara K: "Cell Engineering Biointerface Focusing on Cytocompatibility Using Phospholipid Polymer With an Isomeric Oligo(Lactice Acid) Segment" Biomacromolecules, vol. 6, Apr. 2, 2005, pp. 1797-1802, XP002502025.
Watanabe et al: "Cytocompatible Biointerface on Poly(Lactic Acid) by Enrichment With Phosphotrylcholine Groups for Cell Engineering" Materials Science and Engineering C, Elsevier Science S.A, CH vol. 27, No. 2, Feb. 7, 2007, pp. 227-231, XP005877903 ISSN: 0928-4931.
Kristensen E M E; Nederberg F; Rensmo H; Bowden T; Hilborn J; Siegbahn H: "Photoelectron Spectroscopy Studies of the Funictionalization of a Silicon Surface With a Phosphorylcholine-Terminated Polymer Grafted Onto (3-Aminopropyl)Trimethoxysilane" Langmuir, vol. 22, Oct. 12, 2006, pp. 9651-9657, XP002502026.
Zalipsky S et al.: "Long Circulating, Cationic Liposomes Containing Amino-Peg-Phosphatidylethanolamine" Febs Letters, Elsevier, Amsterdam, NL, vol. 353, No. 1, Oct. 10, 1994, pp. 71-74, XP000858869 ISSN:0014-5793.
Iwasaki et al., "Invitro and ex vivo blood compatibility study of 2-methacryloyloxyethyl phosphorylcholine (MPC) copolymer-coated hemodialysis hollow fibers", Journal of Artificial Organs (2003), 6(4):260-266.
Nakabayashi et al., "Copolymers of 2-methacryloyloxyethyl phosphorylcholine (MPC) as biomaterials", BioMedical Materials and Engineering (2004), vol. 14, 345-354.
Search Report from International Application No. PCT/US08/63147 dated Aug. 4, 2008.
Search Report from International Application No. PCT/US08/63149 dated Aug. 11, 2008.

*Primary Examiner* — Shane Fang

(57) ABSTRACT

The present disclosure provides copolymers including a first monomer including at least one phospholipid possessing at least one hydroxyl group and a second monomer including a cyclic monomer. Compositions, medical devices, and coatings including such copolymers are also provided.

7 Claims, No Drawings

PHOSPHOLIPID COPOLYMERS

CROSS-REFERENCE TO RELATED APPLICATIONS

This application is a continuation in part of U.S. patent application Ser. No. 12/145,605, filed Jun. 25, 2008 which, in turn, claims the benefit of and priority to U.S. Provisional Patent Application No. 60/964,856, filed Aug. 15, 2007, the entire disclosures of each of which are incorporated by reference herein.

TECHNICAL FIELD

The present disclosure relates to copolymers formed utilizing phospholipids as initiators, compositions containing such copolymers, and articles made from or coated with such copolymers or compositions.

BACKGROUND OF RELATED ART

The use of biocompatible materials in forming medical devices and coatings thereon is known. Biocompatible materials may be utilized to improve surface properties of the devices. Examples of surface properties which may be improved include, but are not limited to, cell and protein adhesion, lubricity, drug delivery, protein or DNA delivery, and the like. These materials may also minimize the body's immune response to an implant.

Although present biocompatible materials and coatings on medical devices perform satisfactorily, there is room for improvement in connection with polymers having enhanced properties for the formation of medical devices and coatings thereon.

SUMMARY

Methods for forming copolymers are provided, as well as the resulting copolymers. In embodiments, methods of the present disclosure include contacting at least one cyclic monomer with an initiator including at least one phospholipid possessing at least one hydroxyl group, polymerizing the at least one cyclic monomer, and recovering a resulting copolymer.

Suitable cyclic monomers may include, in embodiments, lactones. Specific examples of suitable cyclic monomers may include, in embodiments, trimethylene carbonate, caprolactone, valerolactone, 1,4-dioxane-2-one, 1,5-dioxepan-2-one, glycolide, lactide, and combinations thereof.

Copolymers of the present disclosure may include, in embodiments, at least one phospholipid including a phosphorylcholine polyol of the following formula:

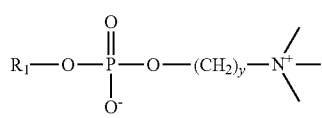

(I)

wherein $R_1$ is a polyol possessing at least one hydroxyl group and y is a number from about 1 to about 10, and at least one cyclic monomer.

In embodiments, copolymers of the present disclosure may include at least one additional monomer such as a polyethylene glycol, polypropylene glycol, polyethylene glycol-polypropylene glycol copolymers, vinyl monomers, silicones, and combinations thereof.

In other embodiments, a copolymer of the present disclosure may include at least one phospholipid including a phosphorylcholine macrodiol of the following formula:

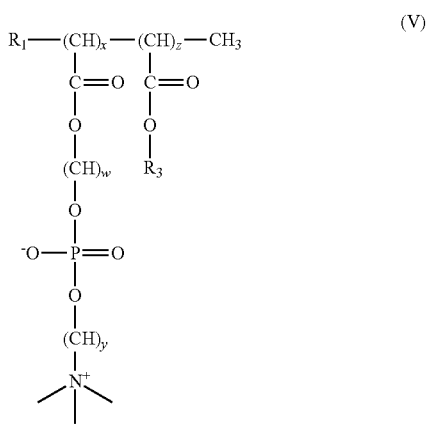

(V)

wherein $R_1$ is a polyol possessing at least one hydroxyl group, $R_3$ is an alkyl group having from about 1 carbon atom to about 10 carbon atoms, w is a number from about 1 to about 6, x is a number from about 250 to about 750, y is a number from about 1 to about 10, and z is a number from about 250 to about 750, and at least one cyclic monomer.

Compositions including a copolymer of the present disclosure are also described. Articles including medical devices which may be made from, or coated with, a copolymer of the present disclosure or a composition including a copolymer of the present disclosure, are also described.

DETAILED DESCRIPTION

The present disclosure provides copolymers including at least one phospholipid monomer possessing at least one hydroxyl group in combination with at least one cyclic monomer, in embodiments a lactone, and compositions including such copolymers.

Copolymers of the present disclosure may possess, as a first monomer, at least one phospholipid possessing at least one hydroxyl group. Such phospholipids are within the purview of those skilled in the art and include, for example, phosphorylcholine diols, phosphorylcholine polyols, phosphorylcholine macrodiols, and combinations thereof. In embodiments, suitable phospholipids for use as the first monomer include phosphorylcholine polyols of the following formula:

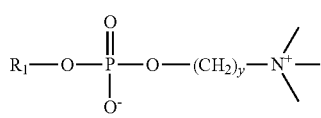

(I)

wherein $R_1$ is a polyol possessing at least one hydroxyl group such as any hydroxyl containing group, including any alcohol, diol, poyol, and the like, as well as any monomer, oligomer polymer, and the like possessing at least one hydroxyl group, and y is a number from about 1 to about 10, in embodiments from about 2 to about 6.

In embodiments, $R_1$ can be of the following formulas:

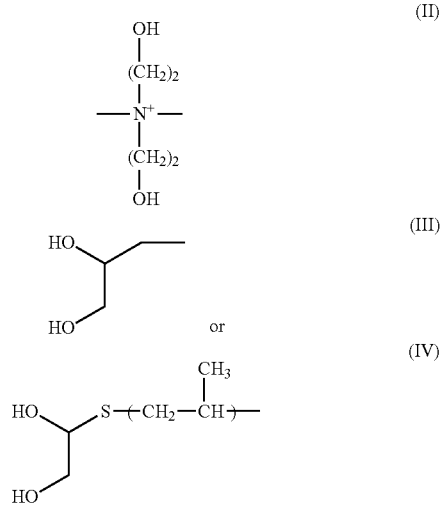

In other embodiments, suitable phospholipids for use as the first monomer include phosphorylcholine macrodiols of the following formula:

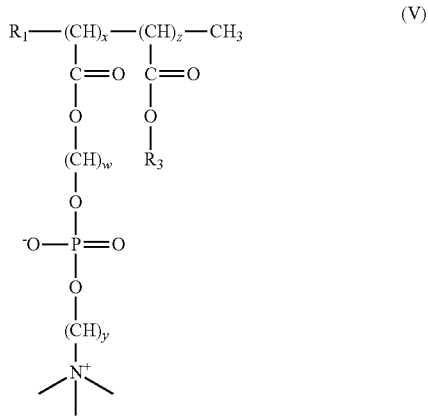

wherein $R_1$ is as defined above, $R_3$ is an alkyl group having from about 1 carbon atom to about 10 carbon atoms, in embodiments from about 3 carbon atoms to about 8 carbon atoms, w is a number from about 1 to about 10, in embodiments from about 2 to about 6, x is a number from about 1 to about 1000, in embodiments from about 250 to about 750, y is a number from about 1 to about 10, in embodiments from about 2 to about 6, and z is a number from about 1 to about 1000, in embodiments from about 250 to about 750.

Examples of other phosphorylcholines which the phospholipid possessing at least one hydroxyl group may be based upon include, but are not limited to, phosphorylcholines such as 2-methacryloyloxyethyl phosphorylcholine (MPC), 2-acryloyloxyethyl phosphorylcholine, and the like, and combinations thereof. Other phosphorylcholines may be utilized, including phosphorylcholines based upon monomers including, but not limited to, 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof. As used herein, "(meth)acryl" includes both methacryl and/or acryl groups.

The copolymers of the present disclosure may be formed by polymerizing the above phospholipid possessing at least one hydroxyl group with a cyclic monomer. Suitable cyclic monomers which may be utilized to form the copolymers of the present disclosure include, but are not limited to, lactones such as trimethylene carbonate, caprolactone, valerolactone, dioxanones including 1,4-dioxane-2-one and 1,5-dioxepan-2-one, glycolide, lactide, and combinations thereof. In some embodiments, for example with caprolactone and 1,5-dioxepane-2-one, their cyclic dimers, which are 14 member lactone rings, can be used instead of the respective monomers.

Conditions for conducting the copolymerization of the above phospholipid possessing at least one hydroxyl group with the cyclic monomers described above are within the purview of those skilled in the art. The conditions under which the at least one phospholipid possessing at least one hydroxyl group may be reacted with the cyclic monomer may vary widely depending on the specific phospholipid, the specific cyclic monomer being employed, and the desired degree of polymerization to be achieved. The amount of phospholipid in the resulting copolymer may be from about 5% to about 90% by weight of the copolymer, in embodiments from about 10% to about 50% by weight of the copolymer, with the cyclic monomer present in amounts form about 10% to about 95% by weight of the copolymer, in embodiments from about 50% to about 90% by weight of the copolymer.

In embodiments, the cyclic monomer and phospholipid possessing at least one hydroxyl group may be combined in the presence of a catalyst such as stannous octoate, sometimes under an inert atmosphere such as nitrogen gas.

In embodiments, the copolymers of the present disclosure may be prepared from monomer solutions prepared by dissolving the cyclic monomer in a suitable solvent, which in embodiments may include the at least one phospholipid possessing at least one hydroxyl group. Suitable solvents which may be utilized include, for example, water, lower alcohols, mixtures of the foregoing, and the like. In other embodiments, an aqueous solution or suspension may be formed of the cyclic monomer in combination with the at least one phospholipid possessing at least one hydroxyl group. In yet other embodiments, the cyclic monomer may be combined with an organic solvent and the resulting solution may then be mixed or emulsified with an aqueous compatible or incompatible solution containing the at least one phospholipid possessing at least one hydroxyl group. Suitable organic solvents include, for example, ethanol, methanol, isopropanol, chloroform, methylene chloride, combinations thereof, and the like.

In addition to preparing the copolymers of the present disclosure, these methods may also be utilized, in embodiments, for surface/bulk modification of devices by impregnating a medical device with monomer solutions of the phospholipid possessing at least one hydroxyl group and/or cyclic monomer, for example by immersion, and in situ polymerizing the monomer solutions to prepare graft copolymers or an interpenetrating network of the copolymers of the present disclosure on or within the medical device.

Solutions may also be used with chemical couplers, for example silanes, vinyl siloxanes, and the like, to not only graft or interpenetrate the surface of a medical device, but to also covalently tether the copolymers of the present disclosure to the surface of a device.

Co-polymerization with other monomers may also be initiated by subjecting the monomers, in embodiments possessing vinyl groups, with, for example, the at least one phospholipid possessing at least one hydroxyl group, to energy including irradiation, such as high energy radiation including gamma and/or e-beam, ultraviolet light, pulse laser ablation deposition, plasma energy treatment, chemical initiation, photoinitiation, positron initiation, and the like.

In embodiments, the use of high energy radiation for initiation may be beneficial as it should not require the use of an additional initiator such as a chemical initiator or catalyst. For example, in some embodiments gamma radiation may be applied in low doses of from about 0.05 Mrad to about 0.5 Mrad, in embodiments from about 0.1 Mrad to about 0.3 Mrad, to initiate polymerization.

Other methods for initiating polymerization are within the purview of those skilled in the art and include, for example, those disclosed in U.S. Pat. Nos. 5,290,548, 5,376,400, 5,804,263, 5,885,566, and 6,387,379, the entire disclosures of each of which are incorporated by reference herein.

Co-polymerization may be carried out in the presence of one or more polymerization initiators, such as benzoyl peroxide, 2,2'-azo-bis(2-methylpropionitrile), benzoin methyl ether, combinations thereof, and the like. Other polymerization initiators which may be used are within the purview of those skilled in the art and include, for example, those disclosed in "Polymer Handbook", 3rd edition, Ed. J. Brandrup and E. H. Immergut, Pub. Wiley-Interscience, New York, 1989.

In embodiments, the phospholipid possessing hydroxyl groups may itself act as an initiator in forming a copolymer of the present disclosure. Thus, in such an embodiment, the phospholipid possessing at least one hydroxyl group may act as an initiator in a ring opening polymerization of the cyclic monomer and polymerize therewith forming a copolymer of the present disclosure, without the need for any additional initiator.

In other embodiments, the resulting copolymer of the present disclosure may possess the phospholipid possessing at least one hydroxyl group in amounts of from about 5 to about 95 percent by weight of the copolymer, in embodiments from about 15 to about 85 percent by weight of the copolymer. Thus, the copolymer of the present disclosure may possess the cyclic monomer in amounts of from about 5 to about 95 percent by weight of the copolymer, in embodiments from about 15 to about 85 percent by weight of the copolymer.

Copolymers of the present disclosure possess many desirable properties, including antimicrobial properties, reduced protein adsorption and cell adhesion, compatibility with blood and biological tissue, and reduced activation of immune cells.

In embodiments, the phospholipid possessing at least one hydroxyl group and the cyclic monomer may also be copolymerized in the presence of additional monomers, including vinyl monomers, polyethylene glycol ("PEG"), polypropylene glycol ("PPG"), PEG/PPG copolymers, silicones, combinations thereof, and the like, to obtain copolymers possessing excellent solubility, wettability, thermal properties, film-forming properties, and the like.

For example, in some embodiments a copolymer of the present disclosure may include a random copolymer of the phospholipid possessing at least one hydroxyl group, the cyclic monomer, and an additional PEG-based monomer or pre-polymer.

In addition to forming copolymers with the phospholipid possessing at least one hydroxyl group and the cyclic monomer, in some embodiments these additional components may be combined with the copolymers of the present disclosure as a mixture or blend. Thus, in embodiments, materials which may be blended with the copolymers of the present disclosure include cyclic monomers, vinyl monomers, PEG, PPG, PEG/PPG copolymers, silicones, and combinations thereof described above, as well as other phospholipids, including phosphorylcholines such as those described above. Where copolymers of the present disclosure are combined with these other monomers and/or phospholipids, such as phosphorylcholines, to produce blends, the copolymers of the present disclosure may act as a compatibilizer to further enhance blending.

Copolymers of the present disclosure may be utilized to form medical devices, drug delivery devices, packaging materials for medical devices, coatings thereon, and the like. In embodiments, copolymers of the present disclosure may be combined with other polymeric materials to form medical devices, drug delivery devices, packaging materials for medical devices, coatings thereon, and the like. Examples of other polymeric materials which the copolymers of the present disclosure may be combined with include, for example, any combination of natural, synthetic, bioabsorbable and/or non-bioabsorbable materials. Some non-limiting examples of materials which may combined with the copolymers of the present disclosure include, but are not limited to, poly(lactic acid), poly(glycolic acid), poly(hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyoxaesters, polyorthoesters, polyphosphazenes, and copolymers, block copolymers, homopolymers, blends and combinations thereof.

In embodiments, suitable materials which may be combined with the copolymers of the present disclosure include homopolymers, copolymers, and/or blends possessing glycolic acid, lactic acid, glycolide, lactide, dioxanone, trimethylene carbonate, caprolactone, and various combinations of the foregoing. For example, in some embodiments, a copolymer of glycolide and trimethylene carbonate may be combined with the copolymer of the present disclosure. Methods for forming these additional copolymers are within the purview of those skilled in the art and include, for example, the methods disclosed in U.S. Pat. No. 4,300,565, the entire disclosure of which is incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments from about 30% to about 35% by weight of the copolymer.

Other suitable materials which may be combined with the copolymers of the present disclosure include, in embodiments, copolymers of glycolide, dioxanone and trimethylene carbonate. Such materials may include, for example, copolymers possessing glycolide in amounts of from about 55% to about 65% by weight of the copolymer, in embodiments from about 58% to about 62% by weight of the copolymer, in some embodiments about 60% by weight of the copolymer; dioxanone in amounts from about 10% to about 18% by weight of the copolymer, in embodiments from about 12% to about 16% by weight of the copolymer, in some embodiments about 14% by weight of the copolymer; and trimethylene carbonate in amounts from about 17% to about 35% by weight of the copolymer, in embodiments from about 22% to about 30% by weight of the copolymer, in embodiments about 26% by weight of the copolymer.

In other embodiments, a copolymer of glycolide, lactide, trimethylene carbonate and ε-caprolactone may be combined with the copolymers of the present disclosure. Such materials may include, for example, a random copolymer possessing caprolactone in amounts from about 14% to about 20% by weight of the copolymer, in embodiments from about 16% to about 18% by weight of the copolymer, in some embodiments about 17% by weight of the copolymer; lactide in amounts from about 4% to about 10% by weight of the copolymer, in embodiments from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in embodiments about 7% by weight of the copolymer; and glycolide in amounts from about 60% to about 78% by weight of the copolymer, in embodiments from about 66% to about 72% by weight of the copolymer, in embodiments about 69% by weight of the copolymer.

The copolymers of the present disclosure may find many uses in the formation of medical devices, drug delivery devices, packaging materials for medical devices, and coatings thereon. In embodiments, surgical articles can be manufactured from the copolymers described herein. Examples of medical devices and/or surgical devices include, but are not limited to, clips and other fasteners, staples, sutures, pins, screws, prosthetic devices, wound dressings, bandages, drug delivery devices, anastomosis rings, surgical blades, contact lenses, anti-adhesion devices, intraocular lenses, surgical meshes, stents, stent coatings, grafts, catheters, stent/grafts, knotless wound closures, sealants, adhesives, tissue scaffolds, stapling devices, buttresses, lapbands, orthopedic hardware, spacers, pacemakers, and other implantable devices. Fibers can be made from the copolymers of the present disclosure. In embodiments, fibers made of copolymers of the present disclosure may be knitted or woven with other fibers, including either absorbable or non-absorbable fibers, to form textiles. The fibers also can be made into non-woven materials to form fabrics, such as meshes and felts.

The present copolymers can be formed into articles using any technique within the purview of those skilled in the art, such as, for example, extrusion, molding and/or solvent casting. The copolymers can be used alone or blended with other polymers, which may be either absorbable or non-absorbable. Copolymers of the present disclosure combined with other materials may be referred to, in embodiments, as compositions of the present disclosure.

Packaging materials which may be formed with the copolymers or compositions of the present disclosure include packaging for products such as medical devices, pharmaceuticals, textiles, consumer goods, foods, and the like.

Copolymers of the present disclosure may also be used to form coatings for articles, including textiles, medical devices, and packaging materials. In embodiments, a coating formed with a copolymer or composition of the present disclosure can be applied as a solution and the solvent evaporated to leave the coating components, in embodiments, the copolymer of the present disclosure, and optionally other materials. Suitable solvents which may be utilized in forming the solution include any solvent or combination of solvents suitable for the chosen coating composition. To be suitable, the solvent must (1) be miscible with the coating components including the copolymer, and (2) not appreciably affect the integrity of any material used to form the article being coated. Some examples of suitable solvents include alcohols, ketones, ethers, aldehydes, acetonitrile, acetic acid, methylene chloride, chloroform and water. In embodiments, methylene chloride may be used as a solvent.

Medical devices and packaging materials in accordance with the present disclosure can then be sterilized in accordance with techniques within the purview of those skilled in the art.

Preparing a coating solution of the present disclosure may be a relatively simple procedure and can be accomplished by blending, mixing, and the like. In one embodiment, where a copolymer of the present disclosure and methylene chloride are utilized to form the coating solution, the desired amount of copolymer may be placed into a container, followed by the addition of the desired amount of methylene chloride. The two ingredients may then be mixed thoroughly to combine the ingredients.

Any technique within the purview of those skilled in the art may be employed for applying the coating solution or suspension to an article. Suitable techniques include dipping, spraying, wiping and brushing. The article wetted with the coating solution or suspension may be subsequently passed through or held in a drying oven for a period of time and at a temperature sufficient to vaporize and drive off the solvent.

A medical device possessing a coating of the present disclosure may also be formed of copolymers of the present disclosure. In other embodiments, medical devices can be formed of other absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable nonabsorbable materials which may be utilized to form the medical device include polyolefins, such as polyethylene, polypropylene, copolymers of polyethylene and polypropylene, blends of polyethylene and polypropylene, polyesters such as polyethylene terephthalate, polymides, polyamides, combinations thereof, and the like.

Textiles which may be coated with copolymer coatings of the present disclosure include fibers made of copolymers of the present disclosure, as well as other natural fibers, synthetic fibers, blends of natural fibers, blends of synthetic fibers, and blends of natural fibers with synthetic fibers. Suitable other materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

As noted above, in embodiments compositions in accordance with the present disclosure may be formed by combining the copolymers with other additional components. In embodiments, coating compositions containing the copolymers of the present disclosure may be combined with a fatty acid component, such as a fatty acid or a fatty acid salt or a salt of a fatty acid ester. Suitable fatty acids may be saturated or unsaturated, and may include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions of the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc oleyl lactylate. In embodiments; calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium oleyl lactylate, lithium oleyl lactylate, potassium oleyl lactylate, rubidium oleyl lactylate, cesium oleyl lactylate, and francium oleyl lactylate. Combinations of the foregoing may also be utilized in embodiments.

In embodiments, a fatty acid component as described above, including a calcium stearoyl lactate, may be combined with a copolymer of the present disclosure or included in any coating solution utilized to apply a copolymer of the present disclosure to a medical article, packaging, textile, and the like.

Where utilized, the fatty acid component can be present in an amount of from about 5 percent to about 60 percent by weight of the total composition including the copolymer of the present disclosure. In embodiments, the fatty acid component may be present in an amount from about 15 percent to about 55 percent by weight of the total composition.

In embodiments, the copolymer can be present in an amount from about 45 to about 60 weight percent of the composition and the fatty acid component, such as a fatty acid salt or a salt of a fatty acid ester, can be present in an amount from about 40 to about 55 weight percent of the composition. In other embodiments, the copolymer can be present in an amount from about 50 to about 55 weight percent of the composition and the fatty acid component can be present in an amount from about 45 to about 50 weight percent of the composition.

In other embodiments, the copolymers of the present disclosure may be combined with additional polymeric materials, such as oligomers and/or polymers. The additional polymeric materials can be bioabsorbable or non-absorbable. Bioabsorbable polymers which may be utilized in compositions including the copolymers of the present disclosure are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof. Similarly, polyorthoesters, polyhydroxy butyrates, polytyrosine carbonates, polyhydroxy alkanoates, combinations thereof, and the like, may be added. The additional polymeric materials may be blended with or bonded to (e.g., to create a block copolymer) the copolymers of the present disclosure.

In embodiments, the copolymers of the present disclosure may be combined with polyalkylene oxides such as polyethylene oxides, polyethylene glycol, polypropylene glycol, copolymers thereof, and the like, including those having acrylate groups such as acrylate PEGs, and/or acrylate PEG/PPG copolymers. Such combinations may include blends or copolymers of the copolymers of the present disclosure with the polyalkylene oxide oligomers or polymers or other non-toxic surfactants. The resulting composition may thus possess antimicrobial properties due to the presence of the copolymers described above. In other embodiments, the copolymers may be combined with silicone acrylates.

If desired, in addition to the copolymers of the present disclosure, compositions described herein can optionally contain additional components, e.g., dyes, antimicrobial agents, growth factors, anti-inflammatory agents, and the like. The term "antimicrobial agent" as used in the present disclosure includes antibiotics, antiseptics, disinfectants and combinations thereof. In embodiments, the antimicrobial agent may be an antiseptic, such as triclosan or one of the cyclic monomers described above.

Classes of antibiotics that can be combined with the copolymers include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam. Other antimicrobials which may be added include, for example, antimicrobial peptides and/or proteins, chemotherapeutic drugs, telomerase inhibitors, other cyclic monomers including 5-cyclic monomers, mitoxanthone, furanones, halogenated furanones, furanone functional polymers and/or copolymers, and the like.

Examples of antiseptics and disinfectants which may be combined with the copolymers include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

In other embodiments, polymer drugs, i.e., polymeric forms of such compounds, for example, polymeric antibiotics, polymeric antiseptics, polymeric non-steroidal anti-inflammatory drugs (NSAIDS), and the like may be utilized. In embodiments, polymer drugs with ester, anhydride, nylon, or urethane linkages may be utilized.

The copolymers of the present disclosure may be combined with various optional ingredients, such as stabilizing agents, thickeners, colors, etc. The optional ingredients may represent up to about 10% of the total weight of the compositions formed with copolymers of the present disclosure.

In embodiments, a medical device in accordance with the present disclosure may be a suture. Sutures in accordance with the present disclosure may be monofilament or multifilament and may be made with the copolymers of the present disclosure or any conventional material, including both bioabsorbable and non-bioabsorbable materials. Suitable materials include, but are not limited to, surgical gut, silk, cotton, polyolefins such as polypropylene, polyamides, polyglycolic acids, polyesters such as polyethylene terephthalate and glycolide-lactide copolymers, and the like.

In embodiments, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolide, lactide, caprolactone, alkylene carbonates (i.e., trimethylene carbonate, tetramethylene carbonate, and the like), dioxanones, orthoesters, hydroxy alkanoates, hydroxybutyrates, tyrosine carbonates, polymide carbonates, polyimino carbonates such as poly(bisphenol A-iminocarbonate) and poly(hydroquinone-iminocarbonate), and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a copolymer of the present disclosure or another suitable material, for example a polyolefin resin, and extruding, drawing and annealing the resin to form the monofilament.

Where the sutures are made of multiple filaments, the suture can be made using any technique within the purview of one skilled in the art such as, for example, braiding, weaving or knitting. The filaments may also be combined to produce a non-woven suture. The filaments themselves may be drawn, oriented, crinkled, twisted, commingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and 6,203,564, the entire disclosures of each of which are incorporated by reference herein. Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, for example, in U.S. Pat. Nos. 3,187,752, 3,565,077, 4,014,973, 4,043,344, and 4,047,533.

In embodiments, a suture in accordance with the present disclosure may be attached to any surgical needle within the purview of those skilled in the art to produce a needled suture. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

Where applied as a coating, in some embodiments the cyclic monomer portion of the copolymer of the present disclosure may act as a tether to attach the phospholipid component of the copolymer to the medical device. In embodiments, the cyclic monomer such as a lactone may thus tether the phospholipid to the device surface which, in embodiments, may project outwardly from the surface of the medical device into a biological environment.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A copolymer comprising:
at least one phospholipid possessing at least one hydroxyl group of the following formula:

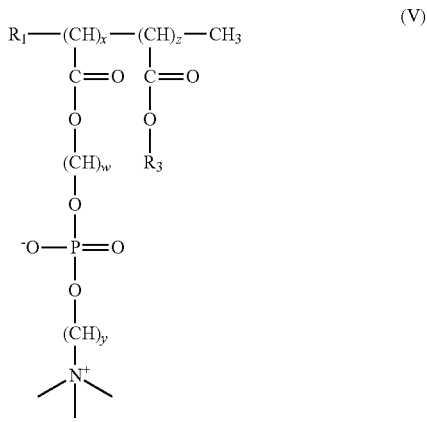

wherein $R_1$ is an alcohol possessing at least one hydroxyl group, $R_3$ is an alkyl group having from about 1 carbon atom to about 10 carbon atoms, w is a number from about 1 to about 10, x is a number from about 250 to about 750, y is a number from about 1 to about 10, and z is a number from about 250 to about 750, and
at least one cyclic monomer.

2. The copolymer of claim 1, wherein the at least one cyclic monomer is selected from the group consisting of trimethylene carbonate, caprolactone, valerolactone, 1,4-dioxane-2-one, 1,5-dioxepan-2-one, glycolide, lactide, and combinations thereof.

3. The copolymer of claim 1, wherein the copolymer possesses the phospholipid in an amount from about 5 percent by weight to about 95 percent by weight of the copolymer, and the cyclic monomer in an amount from about 5 percent by weight to about 95 percent by weight of the copolymer.

4. The copolymer of claim 1, further comprising at least one additional monomer selected from the group consisting of polyethylene glycol, polypropylene glycol, polyethylene glycol-polypropylene glycol copolymers, vinyl monomers, silicones, and combinations thereof.

5. A medical device comprising the copolymer of claim 1.

6. The medical device of claim 5, wherein the copolymer comprises a coating on at least a portion of the medical device.

7. The medical device of claim 5, wherein the medical device is selected from the group consisting of sutures, surgical meshes, anti-adhesion devices, contact lenses, intraocular lenses, staples, clips, buttresses, lapbands, catheters, bandages, stents, grafts, stent/grafts, knotless wound closures, sealants, adhesives, tissue scaffolds, pins, screws, orthopedic hardware, spacers, and pacemakers.

* * * * *